(12) United States Patent
Onwumere

(10) Patent No.: US 6,623,823 B1
(45) Date of Patent: Sep. 23, 2003

(54) RADIOPAQUE POLYMER COATING

(75) Inventor: Fidelis C. Onwumere, Mansfield, TX (US)

(73) Assignee: Ethicon, Inc., Somerville, NJ (US)

(*) Notice: Subject to any disclaimer, the term of this patent is extended or adjusted under 35 U.S.C. 154(b) by 0 days.

(21) Appl. No.: 09/224,463

(22) Filed: Dec. 31, 1998

(51) Int. Cl.⁷ .............. A61F 2/04; A61F 2/06; A61L 29/00; A61M 25/095
(52) U.S. Cl. ............. 428/36.91; 428/35.7; 428/423.3
(58) Field of Search ............. 428/35.7, 423.3, 428/36.91

(56) References Cited

U.S. PATENT DOCUMENTS

| | | | |
|---|---|---|---|
| 3,336,918 A | 8/1967 | Jeckel | 128/2.05 |
| 3,618,614 A | 11/1971 | Flynn | 128/348 |
| 3,749,134 A | 7/1973 | Slingluff et al. | 138/177 |
| 3,901,829 A | 8/1975 | Slingluff et al. | 252/478 |
| 4,182,787 A | 1/1980 | Goossens et al. | 428/36 |
| 4,282,876 A | 8/1981 | Flynn | 128/349 |
| 4,722,344 A | 2/1988 | Cambron et al. | 128/65.8 |
| 4,863,424 A | 9/1989 | Blake, III et al. | 604/54 |
| 5,177,170 A | 1/1993 | Sarpeshkar et al. | 528/76 |
| 5,346,981 A | 9/1994 | Sarpeshkar et al. | 528/85 |
| 6,200,338 B1 * | 3/2001 | Solomon et al. | 623/1.34 |

FOREIGN PATENT DOCUMENTS

EP 452123 10/1991

* cited by examiner

*Primary Examiner*—Sandra M. Nolan
(74) *Attorney, Agent, or Firm*—Blakely, Sokoloff, Taylor & Zafman, LLP

(57) ABSTRACT

An apparatus and method to produce radiopaque medical implants such as catheters, stents, or other implants. A composition of a radiopaque brominated polyurethane coat and a polyurethane tubing core is formed. In one embodiment, the polyurethane coat includes a diisocyanate and a brominated diol having a bromine concentration of 30% or more. The coat is applied to the elastomeric polyurethane tubing core surface. The medical implant takes advantage of employing a brominated radiopaque polyurethane with the tensile properties, for example of flexibility and kink resistance, of the elastomeric thermoplastic polyurethane tubing core without degrading these desirable characteristics.

23 Claims, 1 Drawing Sheet

RADIOPAQUE POLYMER COATING

FIELD OF THE INVENTION

The invention relates generally to medical implants and more particularly to medical implants including surgical tubing or cannulae, for catheters, stents, and other devices.

BACKGROUND OF THE INVENTION

In certain medical procedures, medical implants are placed into the body. These implants include catheters inserted into body passages, vessels, or cavities for passing fluids, draining fluids, making examinations, etc. A stent is a second type of medical implant used to maintain a bodily orifice or cavity during skin grafting or to provide support for tubular structures, for example, during or after anastomosis.

It is generally desirable that medical implants, such as catheters and stents, be radiographically opaque,such that their precise location within the host body can be detected by X-ray examination. In addition, it is advantageous that such medical implant be optically transparent so that a flow of fluid therethrough may be observed.

Many tubular-shaped medical implants, such as catheters and stents are made from a polymer base. The polymers are chosen that can be formed into tubular shapes that are, particularly in the case of catheters, flexible enough to be routed or snaked, to a location in the body. In the case of a peripherally inserted central catheter (PICC), for example, the tubing of the catheter is routed or snaked, in one instance, through a vein in a patient's arm or neck to the superior vena cava of the patient's heart. The tubing must be flexible enough to be routed in this manner without causing trauma to the patient. The polymer chosen as the medical implant should also have sufficient strength when formed into a tubing so that the lumen does not collapse in a passageway or orifice. Still further, the tubing should be resistant to crimping or kinking so that a continuous passageway is assured. Thermoplastic polyurethane-based polymers are a popular choice for medical implant polymers.

In general, polyurethanes are condensation products of reactions between diisocyanate (isocyanate compounds having a functionality of two) and soft-block polyols. Typically, polyurethanes are combined with low molecular weight aliphatic or aromatic diols or diamines as chain extenders to impart the useful elastomeric properties of flexibility, strength, and kink resistance. Low molecular weight diols include butane diol, pentane diol, hexane diol, heptane diol, benzene dimethanol, hydraquinone diethanol and ethylene glycol. Diamines include ethylene diamine, butanediamine, propane diamine and pentane diamine. The diamine based compounds generally form a class of polyurethanes called polyurethaneureas. An added feature of these polyurethanes made with diol or diamine chain extenders is that catheters, stents or vascular grafts formed from these materials are typically optically transparent making these polymer matrices excellent compounds for medical implants. Unfortunately, however, these polyurethanes are generally not radiopaque.

Radiopaque medical implants such as catheters, including radiopaque polyurethanes, have been developed. These radiopaque polymer structures are generally of two forms. A first form of radiopaque polymer incorporates a radiopaque filler or pigment. Typical filler materials include barium sulfate (BaSO4), bismuth subcarbonate, or certain metals such as tungsten (W). Other radiopaque fillers are pigments for incorporation into a polymer tube include bismuth oxychloride and other bismuth salts such as bismuth subnitrate and bismuthoxide (See U.S. Pat. No. 3,618,614). A drawback of the filler incorporated polymers is, although such polymers are radiopaque, the filler tends to make the polymer non-transparent.

A second form of radiopaque polymer useful in medical implants incorporates a halogenated-chain extender into the polymer matrix. Examples of these types of polymers are described in U.S. Pat. Nos. 4,722,344; 5,177,170; and 5,346,981. The preferred halogen in these patents is bromine (Br). Polymers incorporating a brominated-chain extender into the polymer matrix generally yield a tubing that is radiopaque and optically transparent.

In order to impart useful radiopaque properties, the halogenated-chain extended polymer, such as a bromine-chain extended polymer, must have a minimum amount of halogen (i.e., bromine) to impart radiopacity to the polymer. Experimental studies show that the minimum amount of bromine, for example, in a polyurethane-based polymer useful as a catheter, is approximately 15 percent. Amounts less than this tend to make the tubing difficult to detect by X-ray.

A second problem with halogenated-chain extended polymers is the maximum amount of halogen that can be incorporated into the polymer is limited. Experimental studies have shown that polymers having, for example, a bromine concentration greater than 30 percent are too stiff for use as a medical implant, such as a catheter tubing. Accordingly, the radiopacity of the tubing is limited by the amount of bromine that may be incorporated in the polymer matrix without degrading the properties of the tubing made from such a polymer.

As noted above, certain halogenated-chain extended polymers offer both radiopacity and optical transparency. However, in order to maintain the superior elasatomeric properties demonstrated by conventional thermoplastic polyurethane with non-halogenated-chain extenders, the mounts of halogen must be strictly limited. It would be desirable, in certain instances, to have a halogenated-chain extended polymer with a radiopaque property that is not limited by the amount of bromine that is incorporated into the polymer matrix. What is needed is a combination that can maximize the radiopacity of the implant without increasing the halogen concentration of the polymer beyond that which would negatively affect the physical characteristics of the medical implant.

SUMMARY OF THE INVENTION

A method and apparatus to provide improved radiopacity while retaining optical transparency is described. In one embodiment, a tubing is described having a first polyurethane layer and a second brominated polyurethane layer coupled to the first layer.

DETAILED DESCRIPTION

In producing medical implants, the radiopacity of polymer materials, rendered radiopaque by bromination, is limited by the amount of bromine which may be included without altering the properties of the polymer. An apparatus or method which may retain and utilize the flexibility and integrity of the polymer while increasing bromine concentration, and hence radiopacity, finds significant utility.

The invention relates to a radiopaque apparatus, and method for producing such. In one embodiment of the invention a medical implant such as a tubing of a catheter or stent is produced of a polymer-based tubing core and a polymer coat. The polymer core comprises a diisocyanate, a polyol, and a chain extender, which optionally may contain up to 10 percent bromine concentration, though, in an alternate embodiment, no bromine concentration is utilized. In one embodiment, the polymer coat has a bromine concentration of over 30 percent by weight. In one embodiment, the polymer coat comprises a diisocyanate, and a brominated co-monomer. In an alternate embodiment, the polymer coat may include a chemically insignificant amount of a polyol.

Figure 1:
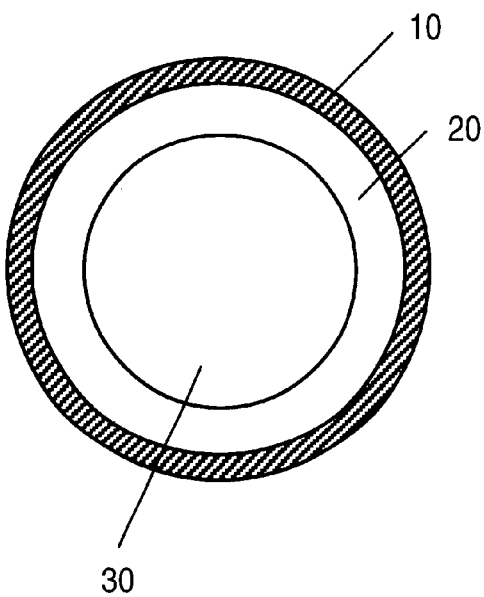
FIGS. 1, 2 and 3 are cross section views of three alternative embodiments of the invention.
Figure 2:
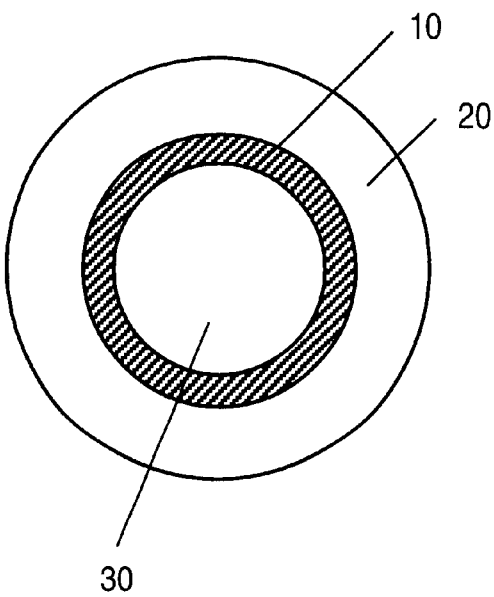
Figure 3:
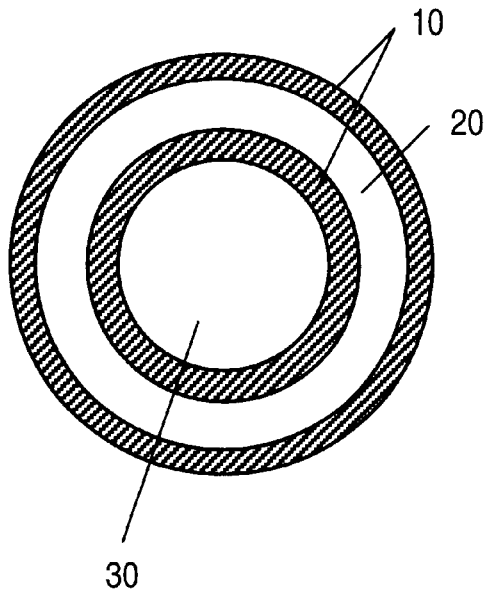

FIG. 1 presents a cross section of a tubing demonstrating application of polymer coat 10 to the outer surface of tubing core 20; (reference numeral 30 represents the tubing lumen). FIG. 2 is also a cross section of a tubing, demonstrating application of the polymer coat to interior surface 10 of the tubing core 20 which form the walls defining lumen 30. FIG. 3 demonstrates a cross section of tubing core 20 coated by polymer coat 10 on both the interior and exterior surfaces.

In one embodiment, the polymer core is in the form of a catheter tubing that is coated by an application of the polymer coat. The manner of coating of polymer core depends on the embodiment. In one embodiment, the polymer coat is separately formed then dissolved in a solvent which is then applied to the polymer core. Solvents for dissolving polymer are well known in the art and include tetrahydrofuran, acetone, dimethlyformamide, dimethylacetamide, methylethyl ketone and cyclohexanone. Upon application, the solvent is removed, in one embodiment by evaporation leaving the polymer coat adhered to the tubing core. In one embodiment, the solvent may be selected to mildly act on the surface of the tubing core to enable adequate bonding between the tubing core and the coating polymer.

In one embodiment, the tubing core is a polymer selected based on its physical and chemical properties. In the case where the tubing core is a polyurethane, the core may comprise a diisocyanate, a polyol, and a chain extender. Methods and procedures for polymerizing and producing such polyurethanes are disclosed in U.S. Pat. Nos. 4,722, 344; 5,177,170; and, 5,346,981. Such technologies are generally understood in the art. The chain extender is, for example, a low molecular weight diol including, but not limited to, ethylene glycol, propylene glycol, hydroquinone bis-hydroxyethylether, butane diol, pentane diol, hexane diol, heptane diol, and benzene dimethanol, and isomers of the same. The chain extender may also be a diamine including, but not limited to ethylene diamine, 1,3-propane diamine, 1,4-butane diamine, 1,5-pentane diamine, 1,6-hexane diamine. The polyol compound of the polyurethane is, for example, polytetrahydrofuran, polyethyleneglycol, ethyeneglycol-b-propyleneglycol-b-ethyleneglycol, polyesterdiol, and polyestercarbonate diol.

A polyurethane such as described above is generally optically transparent. The polyurethane, however, has superior physical properties, including flexibility and a resistance to kinking, making it a popular choice for medical implants such as a tubing of a catheter. In one embodiment, the tubing core, such as a polyurethane as described, also includes a small amount of a halogenated chain extender, particularly a brominated-chain extender. In one embodiment, the tubing core is a polyurethane including a bromine chain extender in amounts less than 10 percent by weight.

One reason to limit the amount of brominated chain extender in the tubing core is to preserve the desirable physical properties of the core-particularly the core's flexibility and elasticity. Significant amounts of brominated chain extender tend to make polyurethane polymers less flexible and therefore less desirable, for example, for use as a catheter tubing.

In one embodiment, the polymer coat is a polyurethane comprising a diisocyanate, and a brominated co-monomer having a bromine concentration greater than about 30 percent, by weight. In prior art compositions, the bromine concentration in the polymer was less than about 30 percent by weight of the polymer due to the potential effect such levels of bromine have on the properties of the polymer and stoichiometric limitations of attaching excess bromine to the polymer. The polymer coat of the invention, however, utilizes a co-monomer having a bromine concentration greater than about 30 percent by weight of the polymer coat as applied to the polymer tubing surface.

Suitable diisocyanates for a polyurethane based polymer coat that may be polymerized with a co-monomer to retain a bromine concentration greater than 30 percent by weight of the polymer coat include, 1,3-diisocyanatopropane, 1,4-diisocyanatobutane, 1,6 diisocyanatohexane, cyclohexanediisocyanate, 1,4-phenylenediisocyanate, tolyenediisocyanate, isophoronediisocyanate, trimethyl 1,6-diisocyanatohexane, 1,3-bis (isocyanatomethyl) benzene, 1,3-bis (isocyanatomethyl) cylcohexane, methylene-bis-diphenyldiisocyanate and methylene-bis-dicyclohexanediisocyanate. Suitable bromine co-monomers according to the invention include, but are not limited to, brominated bisphenol A-diethanol, brominated hydroquinone diethanol, brominated benzene dimethanol, and brominated biphenyloxydiethanol.

In general, the polymer coat is applied to the core in amounts of about 10–50 percent by weight of the apparatus (core & coat). In the embodiment of a polyurethane-based core and a polyurethane-based coat, the increased bromine concentration within the polymer coat and disposed over the surface if the tubing core adheres to the tubing core and increases the radiopacity of the apparatus. While the bromine content of the surface coating only accounts for 10–15 percent of the weight of the entire apparatus (core & coat), its concentration within the coat, at over 30 percent, is significantly higher than the concentration of bromine within polymers used for radiopacity as disclosed by the prior art. Such percentage is, moreover, accomplished without any significant reduction in the elastomeric and flexibility properties of the polymer tubing which need not accommodate a halogen chain extender in its composition.

In one embodiment, a tubing apparatus is provided by thermal extrusion methods generally known in the art. The core is polymerized and extruded into, for example, a tubing core. The polymer coat is prepared by either dissolving the polymerized polyurethane homopolymer composition in a suitable solvent, or by introducing the components of the polyurethane within the solvent individually, (e.g. the brominated co-monomer and the diisocyanate) and initiating polymerization, according to known techniques. The polymer coat is then applied to the tubing core.

An example of the preparation of one embodiment of a certain amount of the polymer coat in a coating composition or solution is to add 63.2 g (0.1 mole) of tetrabromo-bisphenol-A-diethanol to 453 ml of a molecular sieve-dried mixture of approximately even parts acetone and methylethylketone. To this mixture is added 0.02 g of stannous octoate. The mixture is then heated to 50° C. while it is stirred. When the diol has dissolved, 16.8 g (0.1 mole) of 1,6-hexanediisocyanate is added dropwise into the mixture while maintaining the temperature at between 50–55° C. After the addition of the diisocyanate, the mixture is refluxed for eight hours after which time the reaction is complete. This particular preparation contains approximately 15% by weight of the polyurethane homopolymer in the coating composition or solution. The homopolymer composition or solution has a bromine concentration of approximately 6% by weight bromine.

The following table represents various other homopolymers useful in the invention and their corresponding bromine concentration using tetrabromobenzene-1,4-dimethanol and tetrabromobisphenol-A-ethanediol, respectively.

| Diisocyanate | Tetrabromobenzene-1,4-dimethanol Weight % bromine | Tetrabromobisphenol-A-ethanediol Weight % bromine |
|---|---|---|
| 1.3-Diisocyanatopropane | 55.14 | 41.69 |
| 1.4-Diisocyanatobutane | 53.84 | 40.93 |
| 1.6-Diisocyanatohexane | 51.42 | 39.50 |
| Cyclohexanediisocyanate | 51.58 | 39.90 |
| 1.4-phenylenediisocyanate | 52.08 | 39.90 |
| Tolyenediisocyanate | 50.92 | 39.20 |
| Isophoronediisocyanate | 47.29 | 36.99 |
| Trimethyl-1,6-diisocyanatohexane | 48.19 | 37.96 |
| 1,3-bis(isocyanatomethyl) benzene | 49.81 | 38.98 |
| 1,3-bis(isocyanatomethyl) cyclohexane | 49.50 | 38.79 |
| Methylene-bis-diphenyldiisocyanate | 45.42 | 35.83 |
| Methylene-bis-dicyclohexanediisocyanate | 44.66 | 35.34 |

A small quantity of polyol soft segment could be added to the above formulations and still yield a copolymer having a bromine content of more than 35%. Suitable polyols include, but are not limited to poly THF, polyethyleneglycol, ethyleneglycol-b-propyleneglycol-b-ethyleneglycol, polyesterdiol, and polyestercarbonate diol.

Application of the coat to the tubing core may be accomplished, in alternative embodiments, by exposing the interior or exterior surface of the tubing to the polymer solution. In various embodiments, the coat may be applied in a manner consistent with applying polyurethane coats well known in the art. In further embodiments, coating of the interior of, for example, a tubing core may be accomplished by flowing the polymer coat solution through the tubing lumen such that it contacts only the interior surface. Alternatively, the exterior of the tubing core may be sprayed with the polymer coat solution. Also, the tubing core ray be dipped into a bath of polymer coat solution, thereby coating both interior and exterior surfaces of the tubing. In a further embodiment, the exterior surface of the tubing core may be coated by a continuous spooled looping of the tubing core to circulate through a bath of polymer coat. Once the coat solution is applied, drying of the tubing apparatus may be accomplished by air drying or baking.

In the above-described example the coat contained approximately 6% by weight bromine in the homopolymer composition or solution (15% homopolymer). Thus, to produce an apparatus having a coat with a bromine concentration greater than 30% by weight of the coat, several (at least five) coat compositions will be applied in a sequential fashion (i.e., coat, dry, coat, etc.). It is possible to make a coat solution of more than 25% weight polymer which may have a bromine concentration of 12% or more. Even though the viscosity is high, spraying may be used to apply the coating.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A device comprising:
   a polyurethane tubing core; and
   a radiopaque polyurethane coat coupled to the tubing core, said radiopaque polyurethane coat containing greater than 35% by weight bromine.

2. The device of claim 1 wherein the polyurethane tubing core comprises a reaction product of a polymer chain extender, a diisocyanate, and a polyol compound.

3. The device of claim 1 wherein the radiopaque polyurethane coat comprises a reaction product of a diisocyanate and a bromine-containing co-monomer.

4. The device of claim 1, wherein said device is an optically transparent catheter.

5. A method comprising:
   providing a tubing core of polyurethane; and
   coating the tubing core with a bromine-containing radiopaque polymer wherein the coating contains greater than 35% by weight bromine.

6. The method of claim 5 wherein the bromine-containing radiopaque polymer coat is polyurethane.

7. The method of claim 5, wherein the coating comprises:
   dipping the tubing core in a bath of said bromine-containing radiopaque polymer; and
   removing the solvent to deposit a layer of said bromine-containing radiopaque polymer on the tubing core.

8. The method of claim 5, wherein the coating comprises:
   continuously circulating the tubing core within a bath of said bromine-containing radiopaque polymer so as to contact the outside surface of the tubing; and
   removing the solvent to deposit a layer of said bromine-containing radiopaque polymer on the outside surface of the tubing core.

9. The method of claim 5 herein the coating comprises:
   spraying the tubing core with the bromine-containing radiopaque polymer.

10. The method of claim 5 further comprising:
    combining within a solvent a bromine-containing polyurethane comprising a diisocyanate compound and an isocyanate reactive bromine-containing co-monomer compound having a bromine content greater than 35% by weight.

11. The device of claim 1 wherein said radiopaque polyurethane coat comprises 10–50% by weight of a combination of said polyurethane tubing core and said radiopaque polyurethane coat.

12. The device of claim 1 wherein said polyurethane tubing core is not radiopaque and wherein the device is an optically transparent catheter device.

13. The method of claim 5 wherein a tubing core made of non-radiopaque polyurethane is used.

14. The method of claim 5 wherein said polyurethane tubing core comprises an exterior surface and an interior surface.

15. The method of claim 14 wherein the bromine-containing radiopaque polymer coat is applied to said exterior surface of said tubing core.

16. The method of claim 14 wherein said bromine-containing radiopaque polymer coat is applied to said interior surface of said tubing core, which form the walls that define a lumen.

17. The method of claim 14 wherein said bromine-containing radiopaque polymer coat is applied to both said interior surface of said tubing core and said exterior surface of said tubing core.

18. The method of claim 5 wherein said radiopaque polymer coating is formed from a solution containing either (a) 15% of a urethane homopolymer containing 6% bromine or (b) 25% of a urethane homopolymer containing 12% bromine and is applied to the tubing core in a sequential fashion until a desired bromine concentration is achieved.

19. The method of claim 5 wherein said bromine-containing radiopaque polymer coat is prepared by dissolving a polymerized polyurethane homopolymer composition in a suitable solvent.

20. The method of claim 5 wherein said bromine-containing radiopaque polymer coat is prepared by introducing components of said bromine-containing radiopaque polymer coat within a solvent individually and initiating polymerization.

21. A catheter comprising:

a polyurethane tubing core which is not radiopaque; and a radiopaque polyurethane coat coupled to said tubing core, said radiopaque polyurethane coat containing a bromine concentration greater than 35% by weight and wherein said catheter is optically transparent.

22. The catheter of claim 21, wherein said polyurethane tubing core comprises a reaction product of a polymer chain extender, a diisocyanate, and a polyol compound.

23. The catheter of claim 21, wherein said radiopaque polyurethane coat comprises a reaction product of a diisocyanate and a bromine-containing co-monomer.

* * * * *